US009283120B2

(12) United States Patent
Fort (10) Patent No.: US 9,283,120 B2
(45) Date of Patent: Mar. 15, 2016

(54) METHOD FOR APPLYING STRETCHED ELASTIC STRANDS TO A SUBSTRATE

(71) Applicant: Nordson Corporation, Westlake, OH (US)

(72) Inventor: Wesley C. Fort, Cumming, GA (US)

(73) Assignee: NORDSON CORPORATION, Westlake, OH (US)

( * ) Notice: Subject to any disclaimer, the term of this patent is extended or adjusted under 35 U.S.C. 154(b) by 165 days.

(21) Appl. No.: 14/230,728

(22) Filed: Mar. 31, 2014

(65) Prior Publication Data
US 2014/0196836 A1 Jul. 17, 2014

Related U.S. Application Data (62) Division of application No. 13/417,783, filed on Mar. 12, 2012, now Pat. No. 8,720,517.

(51) Int. Cl.
| | | |
|---|---|---|
| B29C 65/48 | (2006.01) | |
| A61F 13/15 | (2006.01) | |
| B65H 57/28 | (2006.01) | |
| B29C 65/52 | (2006.01) | |
| B65H 57/16 | (2006.01) | |
| B05C 5/02 | (2006.01) | |

(52) U.S. Cl.
CPC ..... *A61F 13/15577* (2013.01); *A61F 13/15593* (2013.01); *A61F 13/15609* (2013.01); *B05C 5/0241* (2013.01); *B29C 65/4815* (2013.01); *B29C 65/524* (2013.01); *B65H 57/16* (2013.01); *B65H 57/28* (2013.01); *A61F 2013/1591* (2013.01)

(58) Field of Classification Search
CPC .............. A61F 13/15577; A61F 13/15593; A61F 13/15609; A61F 2013/1591; A61F 2013/49025; B05C 5/0241; B05D 1/26; B29C 65/4815; B29C 65/524; B65H 57/04; B65H 57/16; B65H 57/28
See application file for complete search history.

(56) References Cited

U.S. PATENT DOCUMENTS

| | | | |
|---|---|---|---|
| 4,915,767 | A | 4/1990 | Rajala et al. |
| 4,917,696 | A | 4/1990 | De Jonckheere |
| 5,147,487 | A | 9/1992 | Nomura et al. |
| 5,275,676 | A | 1/1994 | Rooyakkers et al. |
| 5,525,175 | A | 6/1996 | Blenke et al. |
| 6,077,375 | A | 6/2000 | Kwok |
| 7,578,882 | B2 | 8/2009 | Harris et al. |
| 2004/0112983 | A1 | 6/2004 | Saidman et al. |
| 2005/0274318 | A1 | 12/2005 | Bolyard et al. |
| 2006/0251806 | A1 | 11/2006 | Brock et al. |
| 2009/0000545 | A1 | 1/2009 | Bolyard, Jr. et al. |
| 2010/0327074 | A1 | 12/2010 | Bondeson et al. |

FOREIGN PATENT DOCUMENTS

EP 0950436 A2 10/1999

OTHER PUBLICATIONS

European Patent Office, European Search Report in EP Application No. 13156924, Oct. 9, 2013.

*Primary Examiner* — Michael Tolin
(74) *Attorney, Agent, or Firm* — Baker & Hostetler LLP (57) ABSTRACT

A system and method applies a plurality of stretched elastic strands onto a substrate such as along a predetermined non-linear path, to form a leg gather of a disposable absorbent personal hygiene product. The system includes an adhesive dispensing module for individually applying adhesive to the elastic strands. A heated strand guide located downstream of the dispensing module includes guide openings for the respective elastic strands. A drive mechanism coupled to the strand guide actuates movement of the strand guide in a direction transverse to the movement direction of the substrate, thereby causing the elastic strands to be applied to the substrate along the predetermined non-linear path.

5 Claims, 7 Drawing Sheets

METHOD FOR APPLYING STRETCHED ELASTIC STRANDS TO A SUBSTRATE

CROSS-REFERENCE TO RELATED APPLICATION

This application is a divisional of U.S. application Ser. No. 13/417,783, filed Mar. 12, 2012, now U.S. Pat. No. 8,720,517, the disclosure of which is incorporated by reference herein.

FIELD OF THE INVENTION

The present invention generally relates to adhesive dispensing systems and methods and more particularly, to systems and methods for applying curved or non-linear elastic strands to a substrate.

BACKGROUND

Liquid adhesive, such as hot melt adhesive, is applied onto various components during manufacture of disposable absorbent personal hygiene products such as diapers, adult incontinence products, and feminine hygiene products. Dispensing systems have been developed for applying hot melt adhesive onto various components of the disposable absorbent personal hygiene product. In one example, these dispensing systems apply one or more hot melt adhesive filaments to a nonwoven substrate, which is then adhered to one or more thin elastic strands to form an elasticized portion of the disposable absorbent personal hygiene product. Downstream of the dispensing system, the various components (e.g., flat substrate layers and elastic strands) pass through a pressure nip to secure the components together.

Many disposable absorbent personal hygiene products include elasticized leg gathers adjacent to leg openings to secure the personal hygiene product against the user's legs and contain any waste material captured by the personal hygiene product. In these applications, a high level of creep resistance is desirable. "Creep" of an elastic strand is defined as the movement of either end of the elastic strand from an initial location where the end is adhered to a substrate. If an elastic strand undergoes any significant amount of creep after assembly, at least one end of the elastic strand will effectively de-bond from the substrate and reduce the ability of the elasticized portion to remain firmly engaged with the skin surface. To avoid this undesirable creep, a high quality bond must be formed by the adhesive applied to the elastic strand so that the elastic strand does not de-bond from the substrate.

One well understood method of improving the quality of an adhesive bond and thereby reducing creep is by applying additional adhesive on the substrate or the elastic strands. However, applying too much adhesive to an elastic strand locks the elastic strand along its length and thereby reduces the effectiveness of the elastic material to apply force to the substrate. In other words, the elastic strand loses the ability to apply sufficient retraction force to the substrate. Moreover, increasing the amount of adhesive used in disposable absorbent personal hygiene product manufacturing significantly increases cost and also reduces the "hand" or softness of the resulting product. Applying too much adhesive material may also lead to "burn through," which occurs when the adhesive material burns or melts through the adhered substrate. Consequently, the amount of adhesive used to adhere elastic strands to substrates should be minimized while also maintaining a high level of creep resistance, a high retraction force, and minimized burn through and stiffness.

Elasticized leg gathers are formed along opposing side edges of the personal hygiene product. The side edges are generally curved to follow the contour of a leg. It is therefore desirable to apply the one or more elastic strands along a curvilinear path adjacent to the side edges, which improves the fit of the elasticized portion around the legs of a user. To this end, applying non-linear or curved elastic strands to a substrate of the personal hygiene product enables a more comfortable fit and better leakage protection compared to straight elastic strands that do not closely follow the contour of the side edges.

Conventional systems for applying a curved elastic strand to a substrate of a personal hygiene product generally include an oscillating strand roller or guide that must be positioned in close proximity to the substrate so that the stretched elastic strand(s) are applied accurately and under sufficient tension along a desired non-linear path. When multiple elastic strands are applied in each leg gather, the limited clearance between the oscillating strand guide and the substrate also prevents the multiple elastic strands from becoming tangled with one another prior to application to the substrate. The limited clearance is generally on the order of one centimeter, which does not provide enough space for a dispensing module or nozzle to apply adhesive to the elastic strands. Moreover, the high amount of oscillatory movement that would be required for a dispensing module or nozzle to follow the elastic strands in the limited clearance downstream of the oscillating strand guides could apply unacceptably high levels of "g-force" to the dispensing module or nozzle, depending on specific application parameters.

As a result, conventional systems for applying curved elastic strands to a substrate generally apply adhesive along the desired non-linear path on the substrate prior to application of the elastic strand(s) to the substrate. To ensure that the elastic strand(s) are sufficiently adhered to the substrate, an excessively large amount of adhesive must be applied to the desired non-linear path. However, the application of a large amount of adhesive is undesirable for many of the reasons described above, including but not limited to reduced softness or hand, limited force retraction, and increased cost.

There is a need, therefore, for an adhesive dispensing system and method that addresses one or more of these difficulties and reduces the amount of adhesive used to form leg gathers having non-linear elastic strands.

SUMMARY OF THE INVENTION

According to one embodiment, a system for applying adhesive onto a plurality of stretched first elastic strands moving along a machine direction towards a substrate includes a first adhesive dispensing module configured to individually apply adhesive to the first elastic strands. The system also includes a first strand guide having a plurality of first guide openings for respectively receiving the first elastic strands. The first strand guide is positioned downstream from the first adhesive dispensing module and is configured to be positioned proximate to the substrate so that the first elastic strands are adhered to the substrate after passing the first strand guide. The system further includes a first heater with a heating element thermally coupled to the first strand guide for heating the first guide openings to prevent adhesive build up on the first strand guide. The heating element also reheats the adhesive on the first elastic strands before application to the substrate.

In one aspect, the first strand guide further includes a base configured to be coupled to a drive mechanism, a guide arm extending from the base towards the substrate, and a head extending from the guide arm. The head includes the first guide openings and is located sufficiently proximate to the substrate such that a spacing between adjacent first elastic strands is maintained during adherence of the first elastic strands to the substrate. The heater includes a heat pipe coupled to the head of the first strand guide.

In another aspect, the system further includes a drive mechanism coupled to the first strand guide and operative to move the first strand guide in a direction transverse to the machine direction. As a result of the transverse movement, the first elastic strands are applied to the substrate along a predetermined non-linear path. The drive mechanism further includes a first gantry coupled to the first strand guide and mounted for movement in the transverse direction on a stationary guide rod. The drive mechanism also includes a drive shaft coupled to the first gantry and a motorized cam engaging the drive shaft. The cam rotates to move the first gantry in the transverse direction with an oscillating back and forth movement. In some embodiments, the system includes a second strand guide with a plurality of second guide openings for a plurality of stretched second elastic strands. In these embodiments, the drive mechanism actuates mirrored transverse movement of the first and second strand guides towards and away from one another in the transverse direction such that the corresponding first elastic strands and the second elastic strands are adhered to the substrate along reversed predetermined non-linear paths.

In another embodiment according to the invention, a strand guide is used when applying adhesive onto a plurality of stretched elastic strands to be bonded with a substrate as the elastic strands move along a machine direction. The strand guide includes a base, a guide arm extending from the base towards the substrate, and a head extending from the guide arm. The head is located adjacent to the substrate and includes a plurality of guide openings for receiving the elastic strands. The strand guide also includes a heater with a heating element thermally coupled to the head for heating the first guide openings. This heating of the guide openings prevents adhesive build up on the head and reheats the adhesive on the elastic strands before application to the substrate. In one aspect, the plurality of guide openings include comb like guide slots configured to minimize sliding contact between the guide openings and the elastic strands.

In another embodiment, a method of applying a stretched elastic strand onto a substrate includes dispensing adhesive individually onto the stretched elastic strands. The method also includes passing the elastic strands with adhesive through a strand guide as the elastic strands move in a machine direction. The method also includes heating the strand guide to reheat the adhesive before application to the substrate and to prevent adhesive build up on the strand guide as the elastic strands pass through the strand guide. The method further includes adhering the elastic strands to the substrate after passing the elastic strands through the strand guide.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiment given below, serve to explain the principles of the invention.

DETAILED DESCRIPTION OF THE
ILLUSTRATIVE EMBODIMENTS

Figure 1:
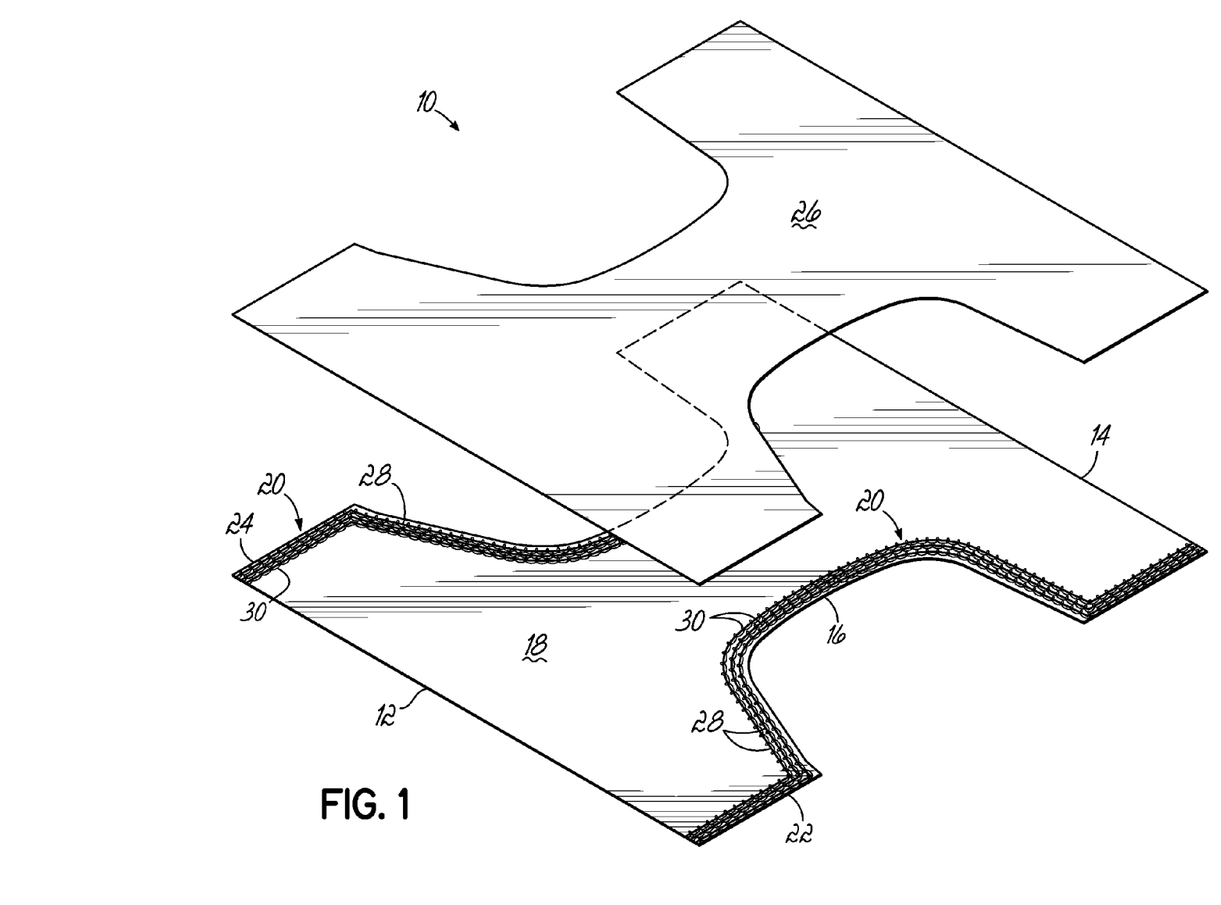
FIG. 1 is a partially exploded perspective view of a disposable absorbent personal hygiene product including elastic strands following a non-linear path in accordance with one embodiment of the invention.

FIG. 1 illustrates one embodiment of a disposable absorbent personal hygiene product 10 manufactured using an illustrative system and method of the invention. The illustrated disposable absorbent personal hygiene product 10 is a disposable diaper 10 including first and second ends 12, 14 configured to wrap around the waist of the user and a narrowed central portion 16 configured to extend between the legs of the user. The diaper 10 includes a flat nonwoven substrate 18, leg gathers 20 formed along each longitudinal side 22, 24 of the diaper 10 between the first and second ends 12, 14, and a second flat substrate 26 secured to the nonwoven substrate 18 to enclose the leg gathers 20. The leg gathers 20 are formed by one or more elastic strands 28 that are secured to the nonwoven substrate 18 in a stretched condition so as to provide the diaper 10 with elasticity around the legs of the user. The second flat substrate 26 is another nonwoven substrate. The nonwoven substrate 18, leg gathers 20, and second substrate 26 are secured to each other with hot melt adhesive 30. As shown in FIG. 1, the elastic strands 28 are secured in a non-linear orientation to the nonwoven substrate 18 so as to follow the longitudinal sides 22, 24 of the diaper 10. More particularly, the non-linear path defined by the elastic strands 28 is a substantially curved path, but it will be understood that this non-linear path may include a plurality of linear sections in other embodiments. Also shown in FIG. 1, the elastic strands 28 are individually coated with adhesive 30 to minimize the total amount of adhesive 30 used to form the leg gathers 20.

Figure 2:
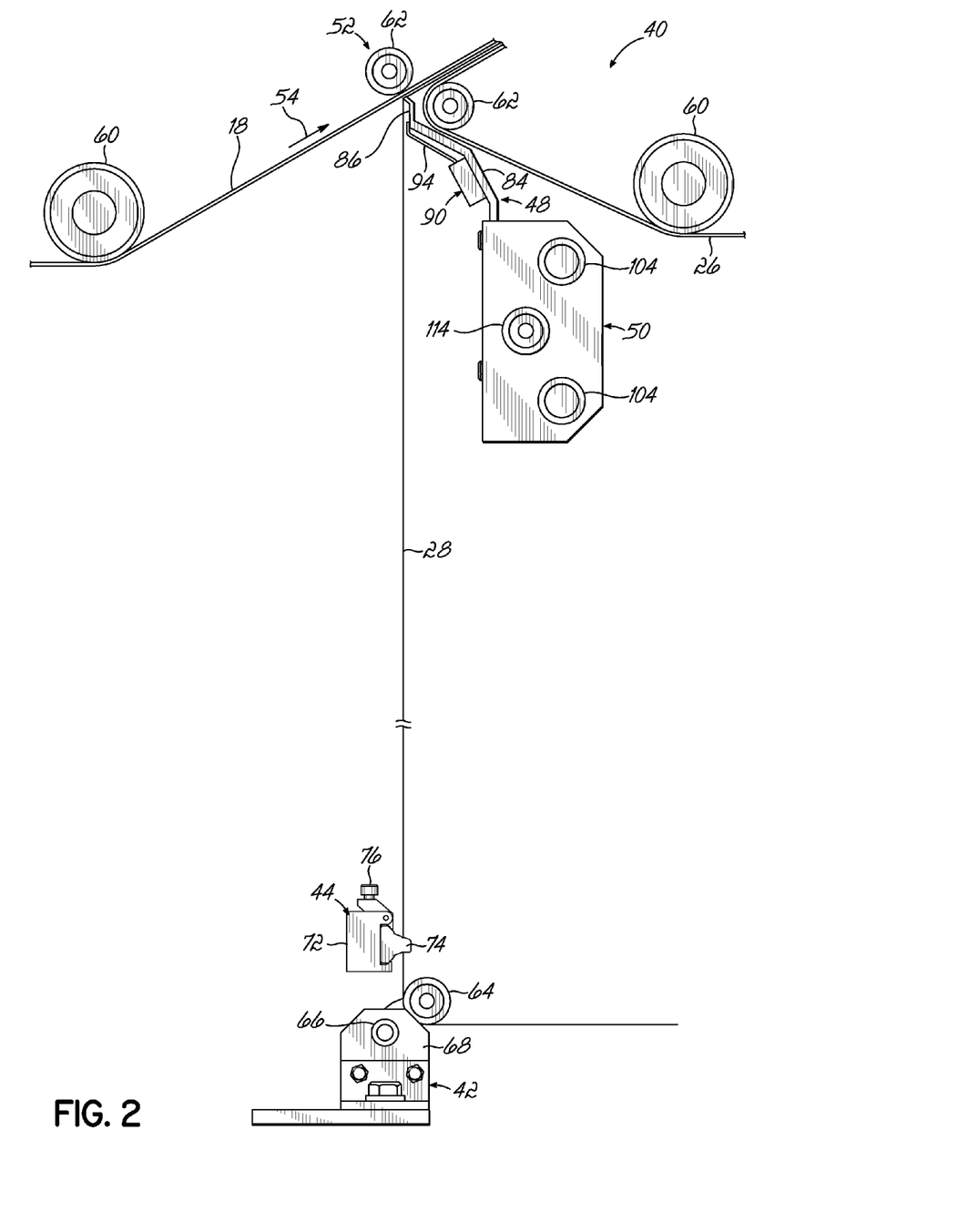
FIG. 2 is a side view of one embodiment of a system for applying elastic strands onto a substrate along a non-linear path.
Figure 3:
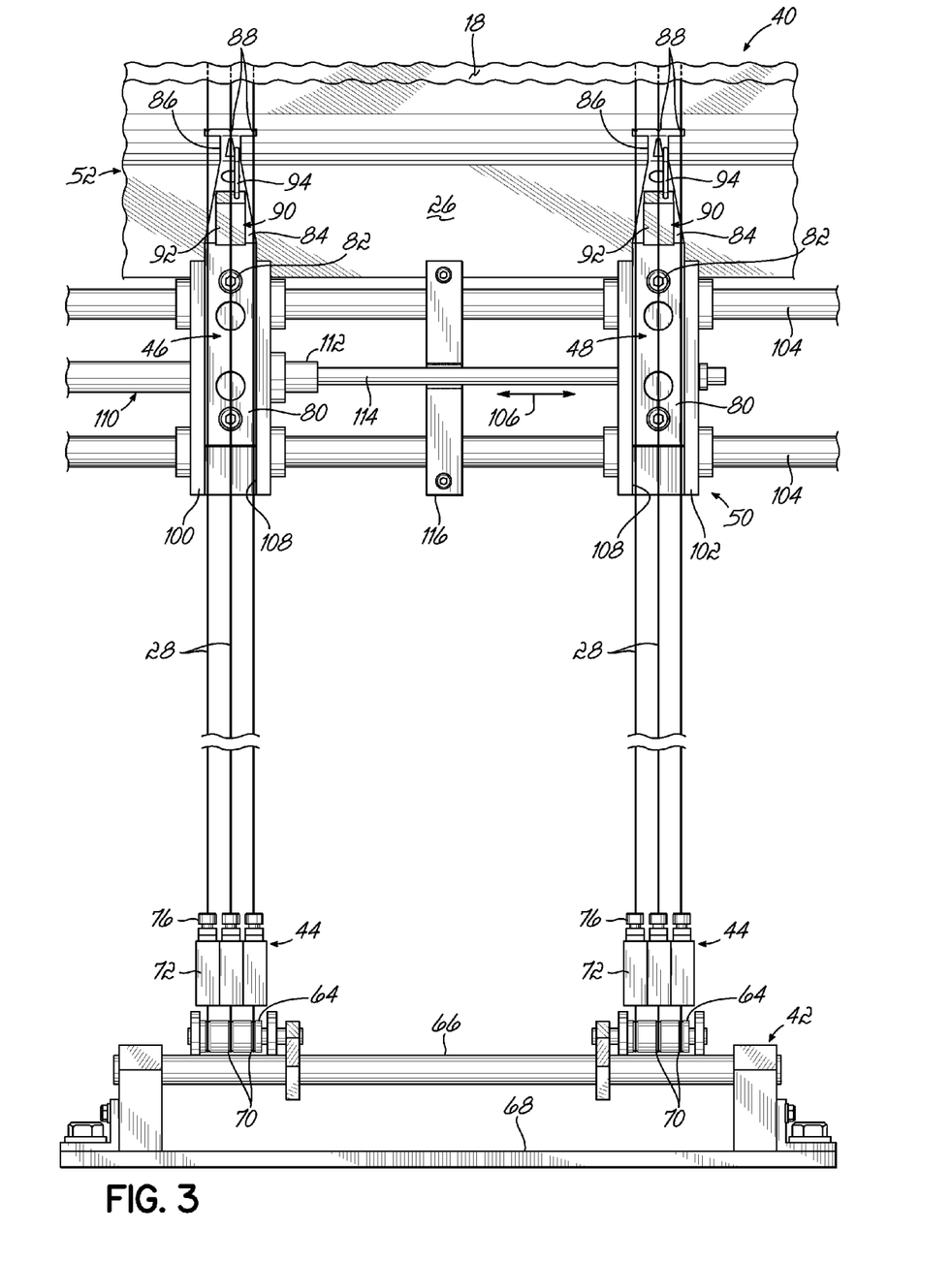
FIG. 3 is a front view of the system of FIG. 2.

An exemplary embodiment of a system 40 in accordance with the invention for applying the elastic strands 28 onto the nonwoven substrate 18 along the non-linear path is illustrated in FIGS. 2-8. With particular reference to FIGS. 2 and 3, the system 40 includes a strand spacer 42 and a plurality of adhesive dispensing modules 44. Downstream of the adhesive dispensing modules 44, the system 40 further includes first and second strand guides 46, 48 coupled to a drive mechanism 50 configured to move the strand guides 46, 48. The first and second strand guides 46, 48 are located in close proximity or adjacent to a bonding device 52, where the elastic strands 28 are applied to the nonwoven substrate 18 and/or the second substrate 26. As a result, the elastic strands 28 on each of the first and second strand guides 46, 48 are applied to the nonwoven substrate 18 with a non-linear, curved pattern as the first and second strand guides 46, 48 translate back and forth with an oscillatory motion transverse to a machine direction indicated by arrow 54.

As shown most clearly in FIG. 2, the bonding device 52 includes supply rollers 60 carrying a continuous sheet of the nonwoven substrate 18 and a continuous sheet of the second substrate 26. The bonding device 52 also includes one or more application rollers 62 that press the elastic strands 28 onto the nonwoven substrate 18 and/or the second substrate 26. As well understood in the art, the bonding device 52 may also include a pressure nip (not shown) to ensure adherence of the elastic strands 28 between the nonwoven substrate 18 and the second substrate 26. It will be understood that the bonding device 52 may alternatively include a folding mechanism that folds a first portion of the nonwoven substrate 18 onto itself and over the elastic strands 28 in other embodiments within the scope of the invention.

With reference to FIGS. 2 and 3, the strand spacer 42 includes a pair of spacing rollers 64 coupled such as by clamping onto a support rod 66 of a support bracket 68. The spacing rollers 64 include a plurality of grooves 70 for receiving incoming elastic strands 28. In this regard, elastic strands 28 running through the grooves 70 are spaced from one another by a desired spacing and remain tensioned before traveling to the dispensing modules 44. The spacing rollers 64 are moveable along the support rod 66 to match the stationary position chosen for the dispensing modules 44. It will be understood that the spacing rollers 64 may include more or fewer grooves 70 depending on the number of elastic strands 28 used to form the leg gathers 20 of the diaper 10, which varies depending upon the diaper 10.

Immediately after passing through the grooves 70 in the spacing rollers 64, the plurality of elastic strands 28 is delivered to one or more dispensing modules 44. The dispensing modules 44 may include any type of contact or non-contact adhesive dispensing module that applies adhesive to elastic strands 28 individually. For example, the dispensing modules 44 shown in the illustrated embodiment are SureWrap® modules commercially available from Nordson Corporation of Westlake, Ohio. To this end, the dispensing module 44 of the exemplary embodiment is a non-contact spiral dispensing module as further described in U.S. Pat. No. 7,578,882 to Harris et al., the entire disclosure of which is hereby incorporated by reference herein. Such a dispensing module 44 generally includes a module body 72 and a nozzle tip 74 removably secured to the module body 72 by a clamping mechanism 76. The nozzle tips 74 apply a filament of adhesive to each elastic strand 28. Alternatively, the dispensing modules 44 could be other non-contact nozzles such as described in U.S. Patent Publication No. 2010/0327074 to Bondeson et al., or other contact nozzles such as described in U.S. Pat. No. 4,917,696 to De Jonckheere, the entire disclosures of which are hereby incorporated by reference herein. In another example, the dispensing modules 44 are roller based contact applicators. Regardless of the type of dispensing module 44 used, the dispensing modules 44 are advantageously mounted so as to be stationary and not affected by any acceleration or "g-forces" during operation of the system 40. The individually coated elastic strands 28 then travel from the dispensing modules 44 to the first and second strand guides 46, 48.

Figure 4:
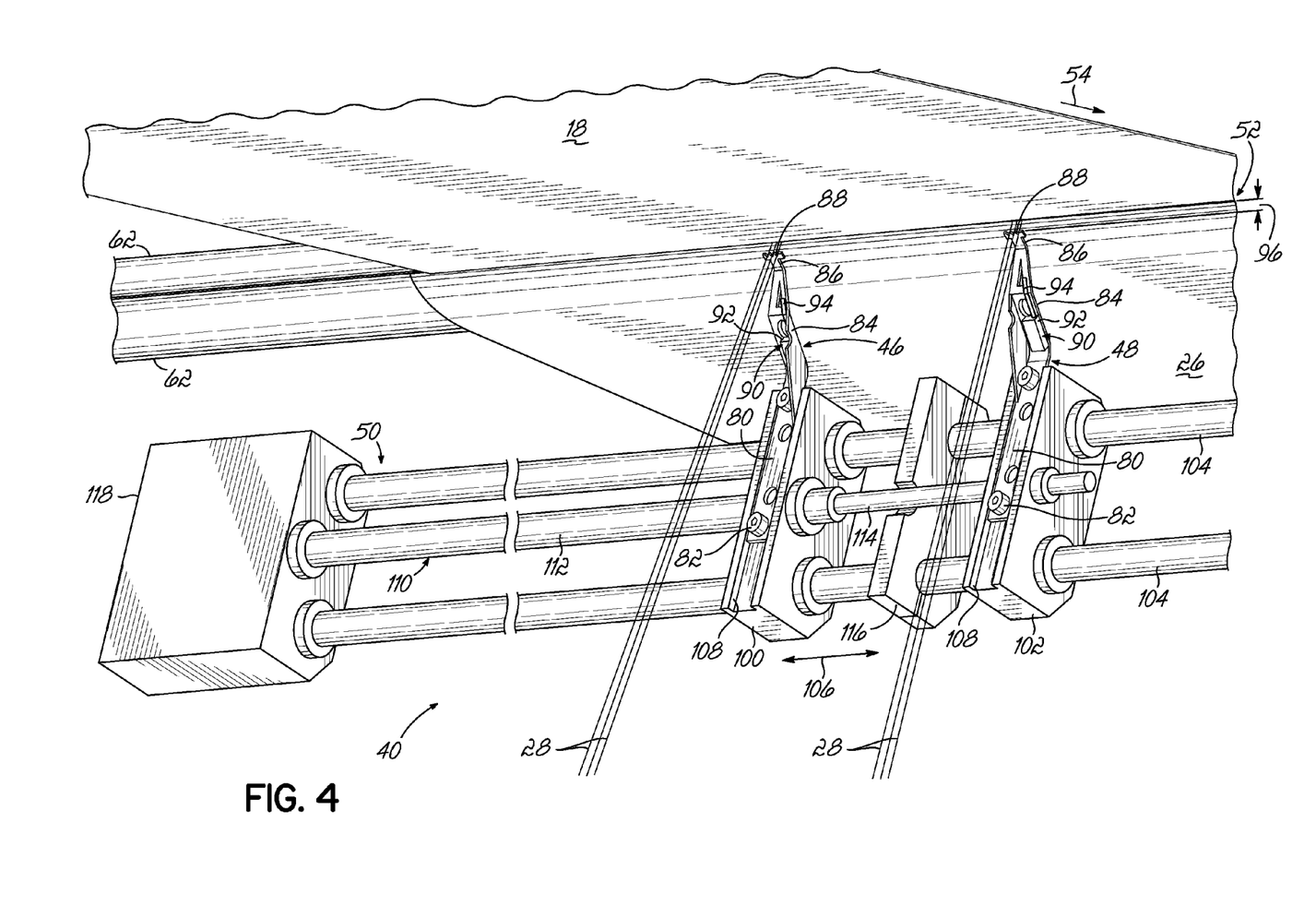
FIG. 4 is a perspective view of the bonding device and the drive mechanism of the system of FIG. 2.
Figure 5:
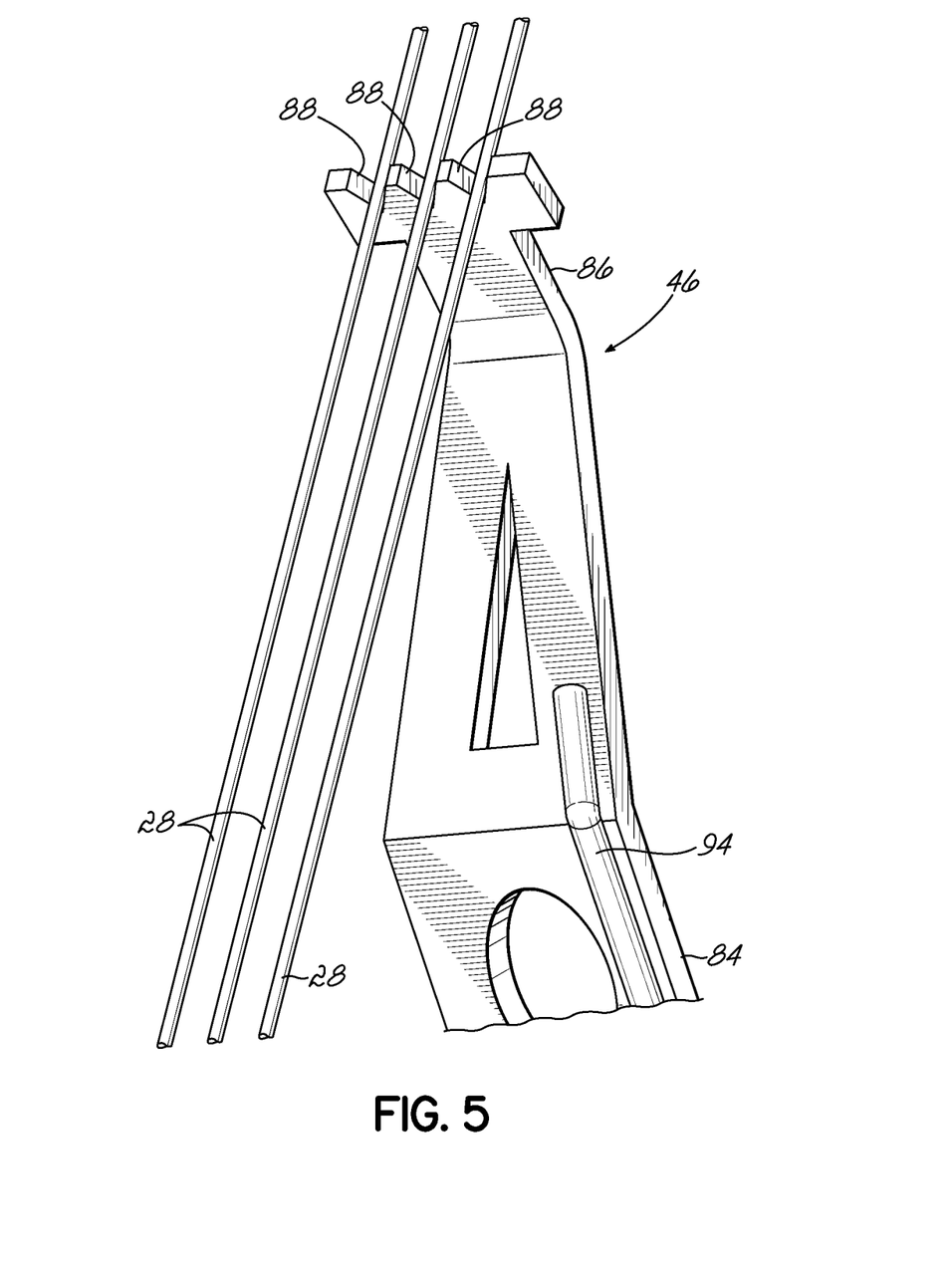
FIG. 5 is a detailed perspective view of one of the strand guides of the system of FIG. 2.

FIGS. 3-5 further illustrate the first and second strand guides 46, 48, which are substantially identical. Thus, the following description of the first strand guide 46 equally applies to the second strand guide 48 as well, and the same elements on the second strand guide 48 are marked with the same reference numbers used below. The first strand guide 46 includes a base 80 coupled to the drive mechanism 50 by one or more fasteners 82. The first strand guide 46 also includes a guide arm 84 extending from the base 80 to a head 86, which is located in close proximity or adjacent to the bonding device 52. In this regard, the guide arm 84 extends from the base 80 towards the bonding device 52. Although the guide arm 84 is shown as including multiple angled portions that taper in transverse width towards the head 86, the specific shape and contour of the guide arm 84 may be modified in other embodiments within the scope of the invention. The head 86 of the first strand guide 46 also includes a plurality of guide openings 88 corresponding to the number of elastic strands 28 passing through the first strand guide 46. Each guide opening 88 is a comb-like guide slot 88 that is substantially wedge-shaped so that the sliding contact between the guide opening 88 and the elastic strand 28 is minimized. The guide openings 88 are spaced from one another by the same spacing set at the spacing roller 64 of the strand spacer 42, thereby maintaining the spacing of the elastic strands 28 near the point of adherence to the nonwoven and/or second substrates 18, 26. It will be understood that the guide openings 88 are shown as guide slots 88 in the exemplary embodiment, but may define apertures, comb-like recesses, or other openings in other embodiments within the scope of the invention.

The first strand guide also includes a heater 90 for heating the head 86 and guide openings 88. In the exemplary embodiment, the heater 90 includes a heater cartridge 92 mounted onto the guide arm 84 adjacent the base 80 and connected to a power supply (not shown). The heater 90 also includes a heating element 94 in the form of a heat pipe 94 extending from the heater cartridge 92 to the head 86 or a location adjacent the junction of the head 86 and the guide arm 84. The heat pipe 94 may be soldered to the head 86 in the exemplary embodiment of the heater 90. The heat pipe 94 transfers heat energy generated by the heater cartridge 92 to the head 86 so that the guide openings 88 are heated substantially to a desired application temperature of the hot melt adhesive 30 on the elastic strands 28. Thus, as the elastic strands 28 pass through the guide openings 88, the heated strand guide 46 reheats adhesive 30 that has cooled in the relatively long distance between the dispensing modules 44 and the first strand guide 46 back to a desired application temperature. It will be understood that the heater 90 may include other types of heat transfer devices such as heat lamps and other types of conductive heaters that are thermally coupled to the strand guide 46 in other embodiments within the scope of the invention.

Additionally, heating the head 86 and the guide openings 88 helps prevent adhesive 30 from building up on the head 86 as the elastic strands 28 pass through the strand guides 46, 48. Over a five minute test run of the system 40 with elastic strands 28 being applied to an entire roll of nonwoven substrate 18, essentially zero adhesive material collected on the head 86 of the first and second strand guides 46, 48. This advantageous result is believed to occur as a result of multiple factors, including the heating of the guide openings 88, the minimized contact between the guide openings 88 and the elastic strands 28, and the high speed of the elastic strands 28 causing a drawing of adhesive 30 away from the guide openings 88. Thus, the elastic strands 28 do not lose substantially any of the hot melt adhesive 30 applied by the dispensing modules 44 as a result of passing through the first and second heated strand guides 46, 48.

As shown most clearly in FIG. 4, the spacing or gap 96 defined between the guide openings 88 in the first and second strand guides 46, 48 and the bonding device 52 is minimized. More specifically, it is critical that this gap 96 be less than two centimeters, and more preferably, less than one centimeter. The minimized gap 96 ensures that the tension or elongation of the elastic strands 28 is substantially maintained at the point of adherence to the nonwoven substrate 18. Moreover, the hot melt adhesive 30 does not have time to cool from the desired application temperature before being applied to the substrate 18, thereby improving the adhesive bond formed between the elastic strand 28 and the substrate 18. The minimized gap 96 also ensures that the spacing between elastic strands 28 is consistently maintained over the entire length of the elastic strands 28.

With continuing reference to FIGS. 3 and 4, the drive mechanism 50 further includes a first gantry 100 and a second gantry 102 mounted for sliding movement on one or more stationary guide rods 104 (two guide rods 104 shown in the Figures). Each of the first and second gantries 100, 102 is configured to move along the guide rods 104 in a transverse direction indicated by arrow 106. Each of the gantries 100, 102 is a plate-shaped member including a groove 108 configured to receive a base 80 of the corresponding strand guide 46, 48. To this end, the first gantry 100 is coupled to the base 80 of the first strand guide 46 and the second gantry 102 is coupled to the base 80 of the second strand guide 48. The drive mechanism 50 also includes a drive shaft 110 fixedly coupled to each of the first and second gantries 100, 102. More particularly, the drive shaft 110 includes an outer drive shaft portion 112 coupled to the first gantry 100 and an inner drive shaft portion 114 coupled to the second gantry 102. The outer and inner drive shaft portions 112, 114 are configured to move independently of one another. Thus, the inner drive shaft portion 114 extends through the entire length of the outer drive shaft portion 112 and beyond the outer drive shaft portion 112 so as to be connected to the second gantry 102. A guard plate 116 is positioned between the gantries 100, 102 to guide the inner shaft portion 114 and to prevent interference of the first and second gantries 100, 102 with each other. The drive shaft 110 extends from the gantries 100, 102 to a motorized cam (not shown in FIGS. 3 and 4), which may be located inside a drive mechanism housing 118 shown in FIG. 4.

Figure 6A:
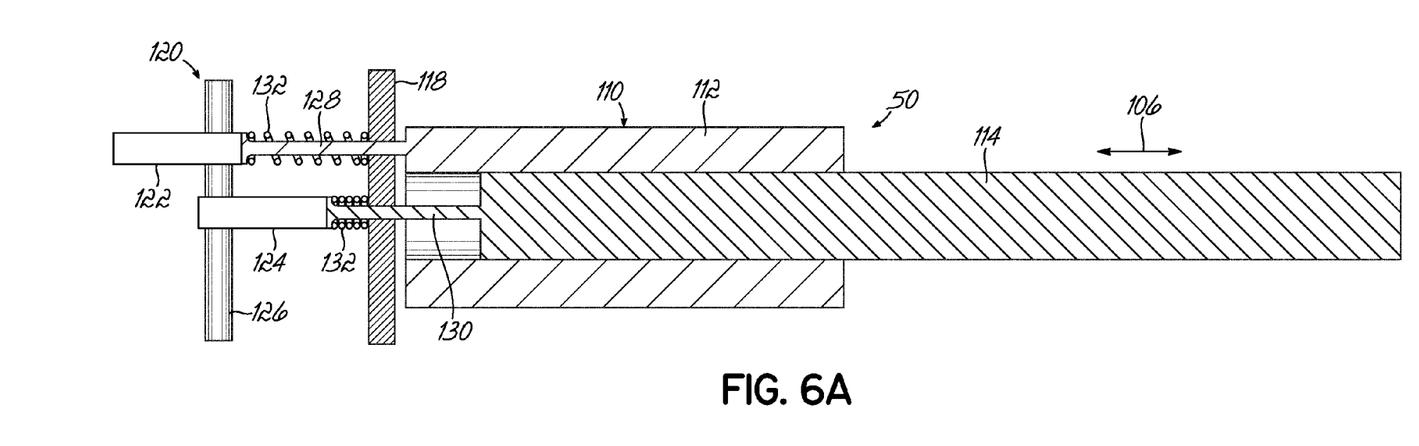
FIG. 6A is a schematic cross-sectional view of the drive mechanism of FIG. 4 in a first position.
Figure 6B:
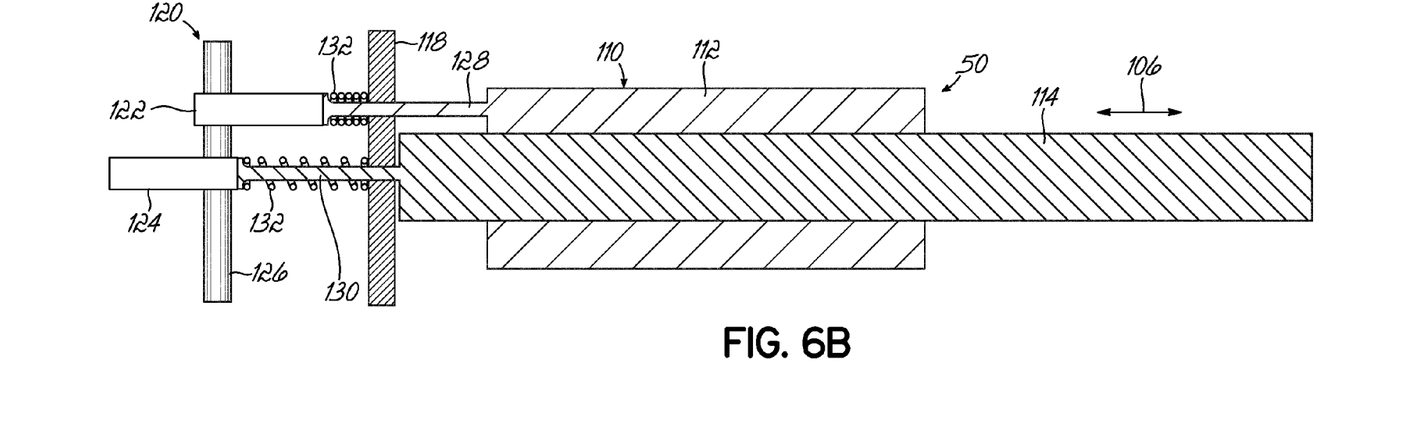
FIG. 6B is a schematic cross-sectional view of the drive mechanism of FIG. 6A in a second position.

The motorized cam 120 located within the drive mechanism housing 118 of the drive mechanism 50 is schematically illustrated in FIGS. 6A and 6B. The motorized cam 120 includes a first cam wheel 122 and a second cam wheel 124 rotatably coupled to a common cam shaft 126. The outer drive shaft portion 112 includes an actuation arm 128 extending through the housing 118 into contact the first cam wheel 122. Similarly, the inner drive shaft portion 114 includes an actuation arm 130 extending through the housing 118 into contact with the second cam wheel 124. Each of the actuation arms 128, 130 is biased into continuous contact with the corresponding cam wheels 122, 124 by springs 132 as shown in FIGS. 6A and 6B. As a result, when the cam shaft 126 rotates to rotate the cam wheels 122, 124, the irregular peripheral profile (not shown) of the first and second cam wheels 122, 124 causes movement of the outer and inner drive shaft portions 112, 114 in the transverse direction.

For example, the outer drive shaft portion 112 is drawn to the left while the inner drive shaft portion 114 is drawn to the right in the first position shown in FIG. 6A, while the outer drive shaft portion 112 is drawn to the right while the inner drive shaft portion 114 is drawn to the left in the second position shown in FIG. 6B. In this regard, the outer and inner drive shaft portions 112, 114 oscillate the first and second gantries 100, 102 in opposite transverse direction to one another. The relative movements of the outer and inner drive shaft portions 112, 114 may be modified from this exemplary embodiment by changing the irregular peripheral profile of the first and second cam wheels 122, 124.

Figure 7:
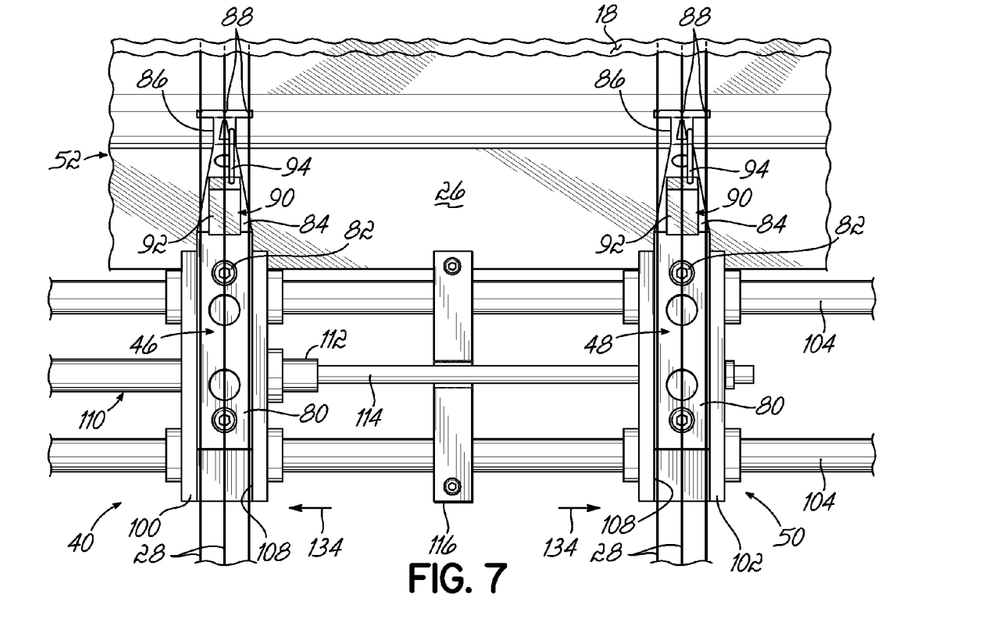
FIG. 7 is a front view of the strand guides and drive mechanism of the system of FIG. 6A in the first position.
Figure 8:
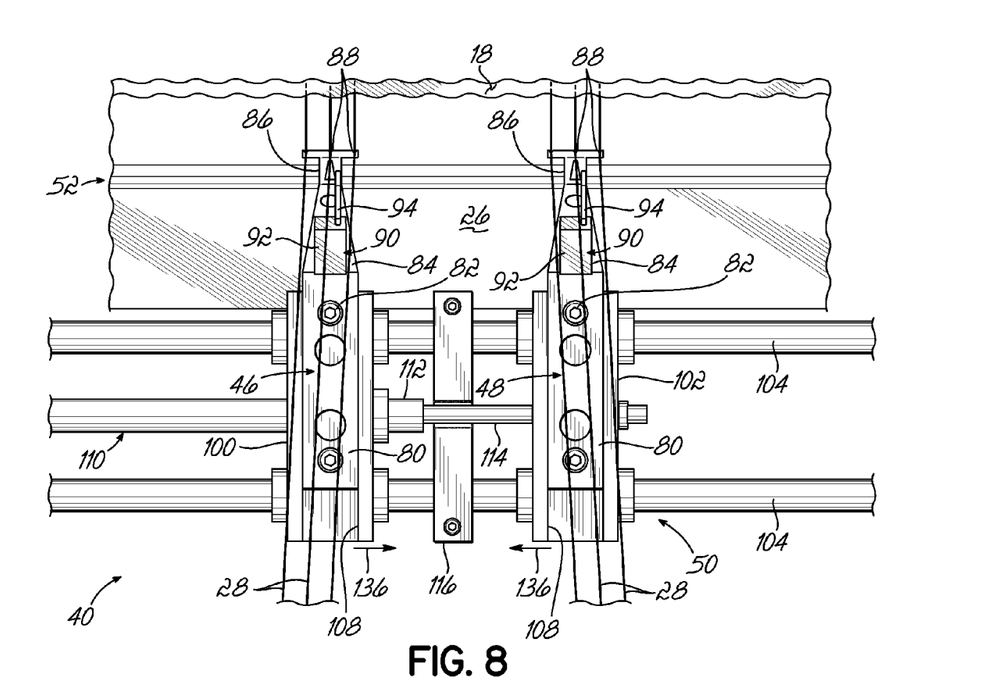
FIG. 8 is a front view of the strand guides and drive mechanism of FIG. 7 in the second position.

The operation of the drive mechanism 50 and the system 40 is further shown in FIGS. 7 and 8. With reference to FIG. 7, the drive mechanism 50 is shown in the first position previously described in FIG. 6A. With reference to FIG. 8, the drive mechanism 50 is shown in the second position previously described in FIG. 6B. To this end, the motorized cam 120 drives the first and second gantries 100, 102 and first and second strand guides 46, 48 away from one another in the transverse direction as shown by arrows 134 in FIG. 7. Then the motorized cam 120 drives the first and second gantries 100, 102 and the first and second strand guides 46, 48 towards each other in the transverse direction as shown by arrows 136 in FIG. 8. In this regard, the drive mechanism 50 may repeatedly cycle or move the gantries 100, 102 transversely between these first and second positions such that the elastic strands 28 are applied in a predetermined non-linear path onto the substrate 18.

For example, the drive mechanism 50 could begin near the first end 12 of a diaper 10 in the spaced apart position shown in FIG. 7, then move the strand guides 46, 48 inwardly to the position of FIG. 8 to follow the longitudinal sides 122, 124 of the central narrowed portion 16, then move the strand guides 46, 48 back outwardly to the position of FIG. 7 to end near the second end 14 of the diaper. Thus, the drive mechanism 50 actuates a reversed transverse movement of the first and second strand guides 46, 48 to produce opposing leg gathers 20 in which the elastic strands 28 follow reversed non-linear paths. As the diapers 10 are generally formed from continuous rolls of substrate 18 and continuous elastic strands 28 that are cut downstream of the bonding device 52, the drive mechanism 50 repeatedly moves the first and second gantries 100, 102 and the first and second strand guides 46, 48 transversely during operation of the system 40. As shown in FIGS. 7 and 8, the deflection or angling in the transverse direction of the elastic strands 28 between the stationary dispensing modules 44 and the bonding device 52 is advantageously minimized as a result of the long distance between the dispensing modules 44 and the bonding device 52.

Consequently, the system 40 is operable to apply a plurality of individually coated elastic strands 28 along one or more predetermined non-linear paths to a nonwoven substrate 18. The heated strand guides 46, 48 ensure that the elastic strands 28 follow the non-linear paths while keeping adequate spacing between adjacent elastic strands 28 and maintaining the adhesive 30 at a desired application temperature. Furthermore, the adhesive 30 remains on the elastic strands 28 as the elastic strands 28 pass through the guide openings 88 of the strand guides 46, 48. The individual application of adhesive 30 to each elastic strand 28 requires less adhesive material than coating an area on the substrate 18 where the elastic strands 28 are to be applied. Thus, the amount of adhesive used to bond the elastic strands 28 to the substrate 18 can be optimized so as to produce desirable levels of creep resistance, product softness, and force retraction. The system 40 therefore produces an advantageous disposable absorbent personal hygiene product 10 with non-linear elastic strands 28 and minimized use of hot melt adhesive 30.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. For example, the strand guides disclosed above may be used in the application of a single elastic strand to a substrate in alternative embodiments. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of applying a plurality of stretched elastic strands onto a substrate, comprising:
    dispensing adhesive individually onto the elastic strands;
    passing the elastic strands with adhesive through a strand guide located proximate to the substrate as the elastic strands move in a machine direction;
    heating the strand guide to reheat the adhesive before application to the substrate and to prevent adhesive build up on the strand guide as the elastic strands pass through the strand guide; and
    adhering the elastic strands to the substrate after passing the elastic strands through the strand guide.

2. The method of claim 1, further comprising:
    moving the strand guide in a direction transverse to the machine direction such that the elastic strands are applied to the substrate along a predetermined non-linear path.

3. The method of claim 2, wherein the strand guide is coupled to a gantry of a drive mechanism, which also includes a drive shaft coupled to the gantry and a motorized cam, and the method further comprises:
    rotating the cam to move the drive shaft, the gantry, and the strand guide along the transverse direction.

4. The method of claim 3, wherein rotating the cam further comprises:
    rotating the cam to oscillate the gantry and the stand guide back and forth along the transverse direction.

5. The method of claim 3, wherein passing the elastic strands through the strand guide further comprises:
    setting a spacing between adjacent elastic strands, the spacing being maintained during adherence of the elastic strands to the substrate.

* * * * *